United States Patent
Cheung et al.

(10) Patent No.: US 9,833,544 B2
(45) Date of Patent: Dec. 5, 2017

(54) BIPHASIC COLLAGEN MEMBRANE OR CAPSULE FOR GUIDED TISSUE REGENERATION

(71) Applicant: Osseous Technologies of America, Newport Beact, CA (US)

(72) Inventors: David Cheung, Arcadia, CA (US); William Knox, Newport Beach, CA (US); Jay Malmquist, Portland, OR (US); Edwin Shors, Laguna Beach, CA (US); Dennis Smiler, Encino, CA (US)

(73) Assignee: OSSEOUS TECHNOLOGIES OF AMERICA, Newport Beach, CA (US)

( * ) Notice: Subject to any disclaimer, the term of this patent is extended or adjusted under 35 U.S.C. 154(b) by 689 days.

(21) Appl. No.: 14/082,035

(22) Filed: Nov. 15, 2013

(65) Prior Publication Data
US 2014/0072747 A1 Mar. 13, 2014

Related U.S. Application Data

(63) Continuation of application No. 13/148,261, filed as application No. PCT/US2010/023275 on Feb. 5, 2010, now abandoned.
(Continued)

(51) Int. Cl.
*A61L 27/24* (2006.01)
*A61L 27/36* (2006.01)
(Continued)

(52) U.S. Cl.
CPC .............. *A61L 27/24* (2013.01); *A61L 27/36* (2013.01); *A61L 27/3633* (2013.01); *A61L 27/56* (2013.01); *A61L 27/58* (2013.01); *A61L 27/60* (2013.01); *A61L 31/044* (2013.01); *A61L 31/12* (2013.01); *A61L 31/146* (2013.01); *A61L 31/148* (2013.01); *B32B 1/02* (2013.01); *B32B 1/08* (2013.01); *B32B 5/06* (2013.01); *B32B 5/14* (2013.01); *B32B 5/18* (2013.01); *C07K 14/78* (2013.01); *Y10T 428/139* (2015.01); *Y10T 428/1348* (2015.01); *Y10T 428/1352* (2015.01); *Y10T 428/1372* (2015.01);
(Continued)

(58) Field of Classification Search
CPC ...... A61L 27/24; A61L 27/36; A61L 27/3633; A61L 27/56; A61L 27/58; A61L 27/60; A61L 31/044; A61L 31/12; A61L 31/146; A61L 31/148; A61L 27/365; B32B 1/02; B32B 1/08; B32B 5/06; B32B 5/14; B32B 5/142; B32B 5/145; B32B 5/18; B32B 2317/10; Y10T 428/1348; Y10T 428/1352; Y10T 428/1372; Y10T 428/1376; Y10T 428/139; Y10T 428/1393
See application file for complete search history.

(56) References Cited

U.S. PATENT DOCUMENTS 2,936,229 A 5/1960 Shepard
3,422,181 A 1/1969 Chirgwin, Jr.
(Continued)

*Primary Examiner* — Walter B Aughenbaugh
(74) *Attorney, Agent, or Firm* — Birch, Stewart, Kolasch & Birch, LLP

(57) ABSTRACT

A biocompatible, resorbable biphasic collagen membrane having a first area of relatively higher tensile strength and stiffness and lower porosity and a second area of relatively lower tensile strength and stiffness and higher porosity, and a method of manufacturing the such a membrane.

4 Claims, 1 Drawing Sheet

Related U.S. Application Data

(60) Provisional application No. 61/150,555, filed on Feb. 6, 2009.

(51) Int. Cl.

| | | |
|---|---|---|
| *A61L 31/12* | (2006.01) | |
| *A61L 27/56* | (2006.01) | |
| *B32B 1/02* | (2006.01) | |
| *B32B 5/06* | (2006.01) | |
| *A61L 27/60* | (2006.01) | |
| *A61L 27/58* | (2006.01) | |
| *B32B 5/14* | (2006.01) | |
| *B32B 1/08* | (2006.01) | |
| *B32B 5/18* | (2006.01) | |
| *A61L 31/04* | (2006.01) | |
| *A61L 31/14* | (2006.01) | |
| *C07K 14/78* | (2006.01) | |

(52) U.S. Cl.
CPC .... *Y10T 428/1376* (2015.01); *Y10T 428/1397* (2015.01); *Y10T 428/24942* (2015.01)

(56) References Cited

U.S. PATENT DOCUMENTS

| | | |
|---|---|---|
| 3,428,584 A | 2/1969 | Riley |
| 4,624,673 A | 11/1986 | Meyer |
| 5,162,506 A | 11/1992 | Hadden |
| 5,512,291 A | 4/1996 | Li |
| 5,955,110 A * | 9/1999 | Patel .............. A61F 2/0063 424/551 |
| 5,997,896 A | 12/1999 | Carr, Jr. et al. |
| 7,112,417 B2 * | 9/2006 | Vyakarnam ......... A61F 2/30756 424/422 |
| 2002/0119437 A1 | 8/2002 | Grooms et al. |
| 2003/0203008 A1 * | 10/2003 | Gunasekaran ......... C07K 14/78 424/442 |
| 2005/0096734 A1 | 5/2005 | Majercak |
| 2007/0198059 A1 * | 8/2007 | Patel ................ A61L 27/3604 606/213 |
| 2008/0206297 A1 | 8/2008 | Roeder et al. |
| 2008/0262630 A1 | 10/2008 | Fulmer et al. |

\* cited by examiner

BIPHASIC COLLAGEN MEMBRANE OR CAPSULE FOR GUIDED TISSUE REGENERATION

CROSS REFERENCE TO RELATED APPLICATIONS

This application is a Continuation of co-pending application Ser. No. 13/148,261 filed on Feb. 22, 2012, which claims priority to PCT International Application No. PCT/US2010/023275 filed on Feb. 5, 2010, which claims the benefit of U.S. Provisional Application No. 61/150,555 filed on Feb. 6, 2009. The entire contents of all of the above applications are hereby incorporated by reference.

FIELD OF THE INVENTION

The present invention relates to a biphasic collagen membrane for guided tissue regeneration in a human or other mammal.

BACKGROUND OF THE INVENTION

Collagen has been used as an implantable biomaterial for more than 50 years. The collagen used for biomedical implants is either derived from animals (e.g., cows, pigs, horses) and humans, or it is manufactured in vitro using recombinant engineering. It is known to be biocompatible and is resorbed and remodeled like natural tissues, via cellular and enzymatic processes. Conventional collagen implants typically have been made of highly porous, reconstituted bovine (i.e., cow) collagen. These collagen implants are commercially sold to surgeons as rectilinear sheets with uniform thicknesses and porosity. Their low density and high porosity make these collagen membranes supple and conformable. Unfortunately they therefore have inadequate tensile strength and stiffness, particularly after wetting with saline or blood, for use as a containment device in surgical applications.

Bone is the body's primarily structural tissue; consequently it can fracture and biomechanically fail. Fortunately, it has a remarkable ability to regenerate because bone tissue contains stem cells which are stimulated to form new bone within bone tissue and adjacent to the existing bone. Boney defects regenerate from stem cells residing in viable bone, stimulated by signally proteins, and multiplying on existing cells or on an extracellular matrix (i.e., trellis). Like all tissues, bone requires support via the vascular system to supply nutrients and cells, and to remove waste. Bone will not regenerate without prompt regeneration of new blood vessels (i.e., neovascularization), typically with the first days and weeks of the regenerative cascade.

Various attempts have been made in the past to stimulate or augment bone regeneration by introducing a bone regenerating material proximate a deteriorated bone structure. Such efforts have met with very limited success, however, because they have not been able adequately to control the placement of the bone regenerating material and thus guide the development of new or additional bone. Measures undertaken to control the placement of the bone regenerating material may hinder cell ingrowth and formation of blood vessels needed for development of additional bone and thus impede the desired bone regeneration. Thus, despite considerable efforts of the prior art, there has remained a long felt need for better methods of tissue augmentation, especially for bone regeneration or augmentation.

SUMMARY OF THE INVENTION

The present invention provides a sheet or membrane of resorbable collagen which may be used by surgeons as an implantable medical device to aid in a variety of tissue regenerative indications. Heretofore, sheets or membranes of collagen have been either highly porous and biomechanically weak or they have been minimally porous and biomechanically strong. For many tissue regenerative indications, it is desirable to have the sheets or membranes of collagen with areas of high strength and stiffness, and at the same time with other areas of high porosity. High strength and stiff collagen provides structure for containing or retaining cells, growth factors or particulate matrices; however low porosity precludes the ingrowth of blood vessels and regenerative cells. Highly porous collagen permits essential ingrowth but does not contain or retain cells, growth factors or particulate matrices at a targeted location. The present invention provides a resorbable biomaterial for guided tissue regeneration which is biphasic, with selected areas designed for high strength and other areas designed for high porosity. The invention thus provides a biocompatible and resorbable collagen membrane, sheet or capsule with biphasic collagen for guided tissue regeneration which is ideal for many bone reconstructive indications.

The membranes or sheets of the invention serve four functions. First, they serve as a trellis for tissue regeneration. Second, they serve as a barrier for separating tissues. Third, they serve as a biocompatible structural material for containing biomaterials at a desired location and/or in a desired configuration. Fourth, they serve as load bearing materials, typically in tension.

Trellises of porous biomaterials (i.e., matrices) serve as a framework on which and through which tissue can grow. Most tissues, including bone, proliferate only by attaching to a structure or matrix. Cells then multiply and expand on pre-existing cells, extra-cellular matrix or biomaterials. Therefore, these matrices must have porosity. However, porosity generally decreases strength, typically non-linearly such that a small amount of porosity disproportionally decreases mechanical properties. The optimal porosity has been characterized in the musculoskeletal, field, for various principal regenerative tissues. For neovascular tissue (i.e., new blood vessels), pore diameters must be larger than 20 micrometers. For osteoid (non-mineralized bone), pore diameters must be larger than 50 micrometers. For bone formation, pore diameters must be larger than 100 micrometers.

Tissue regeneration is a race between competing tissues. Whichever tissue fills the space first, will dominate. Fibrovascular tissues proliferate faster than bone tissue. Consequently, fibrovascular tissue can preferentially fill in a defect where bone is desired, resulting in scar tissue. The present inventors have discovered that a membrane of collagen according to the invention can block the fibrovascular tissue, giving more time for bone formation to occur. Therefore, by using biocompatible, resorbable membranes according to the present invention as barriers to tissue regeneration, bone surgeons can exclude fibrovascular (i.e., scar tissue) from bone defects.

Assuring precise positioning of implanted tissue augmentation materials in a living body can be a difficult task. Moreover, because a living body is a dynamic environment, implanted materials may shift in position over time. The use of strategically shaped and implanted membranes according to the present invention, however, facilitates precise placement of implanted biomaterials and enables containment or retention of the implanted biomaterial at the desired location within the body. The present invention makes use of collagen as a resorbable biomaterial for implantable medical devices to aid in tissue regeneration and repair. Depending on the extent of cross linking, collagen biomaterials can be manufactured to resorb over a prescribed range, typically from 6 weeks to one year. The present invention uses collagen membranes with three dimensional shapes to facilitate tissue regeneration, particularly bone. These three dimensional shapes are manufactured by casting collagen in male and female molds and lyophilizing, to form a highly porous structure. The collagen membranes are then collapsed and cross linked to provide high strength, stiff membranes. Collagen membranes can be formed into a variety of three dimensional shapes, such as capsules, wedges or balloons. For example, capsules can be formed to contain and retain bone grafting materials to their desired location. These capsules can aid in the reconstruction of the buccal plate after tooth extraction. Early models of such capsules, however, were monophasic. For maximum effectiveness, the capsules must have adequate porosity for ingrowth of blood vessels and bone cells. To provide pores for neovascular ingrowth, in some instances it has been necessary for a surgeon to intra-operatively cut and shape the membranes. This shaping is time consuming, inaccurate and compromising to mechanical function (i.e., graft containment) of the three dimensional shapes. The present invention solves this need by providing biphasic collagen membranes for guided tissue regeneration.

The biphasic collagen membranes or capsules for guided tissue regeneration in accordance with the present invention may be produced by the following processes. Three dimension shapes of collagen membranes can be manufactured by a casting process using male/female molds. The space between the molds is filled with a collagen suspension. Macroscopic holes can be made in the membrane with strategically placed pins transecting the mold cavity. After lyphilization, the pins are removed and the mold is decoupled. The membrane can then be rehydrated and dried to provide a high strength three dimensional form. This process provides membranes with one portion of the surface contains transmembrane, unidirectional holes and another portion without porosity, but with high strength and stiffness.

Three dimension shapes of collagen membranes can be manufacturing using male/female molds and the following penetration process. The space between the molds is filled with a collagen suspension. After lyphilization, the membrane can then be rehydrated and dried to provide a high strength three dimensional form. Macroscopic holes can then be made in the membrane with strategically placed pins, cuts, or laser cutting. This process provides membranes in which one portion of the surface contains transmembrane, unidirectional holes and another portion is free of porosity, but exhibits high strength and stiffness.

Biphasic collagen membranes can also be made by a selective rehydration/drying process. Three dimension shapes of collagen membrane are first manufactured using male/female molds by filling the space between the molds with collagen suspension. After lyphilization, a selected portion of the porous membrane is rehydrated and dried to provide a high strength three dimensional form. The remaining portion that is not rehydrated/dried retains an open porosity, but has a lower strength and stiffness. This process provides membranes with one portion of the membrane contains interconnected porosity with relatively low stiffness and another portion of the membrane has high stiffness and low porosity.

The biphasic collagen membrane or capsule of the invention has a number of important advantages for guided tissue regeneration. The membrane or capsule of the invention exhibits optimal porosity. The membrane or capsule of the invention assures that the optimal porosity is provided in collagen membranes to assure neovascular ingrowth and bone cell ingrowth because pores of the required dimensions are precisely manufactured.

The biphasic collagen membrane or capsule of the invention also exhibits optimal strength. The membrane or capsule of the invention assures that the optimal mechanical properties are provided in collagen membranes so that they will deposit bone graft materials at the optimal location at retain the deposited materials at that location.

The biphasic collagen membrane or capsule of the invention also provides convenience for the surgeon who uses it. Although a surgeon could make holes in conventional collagen membranes, the precision and continuity of the holes in the membrane or capsule of the invention would be difficult for a surgeon to replicate with typical surgical tools. Moreover, if the surgeon attempts to form perforations in the membrane, the membranes may be excessively cut or penetrated to an extent that causes it to lose the desired mechanical attributes (i.e., graft containment, tissue separation). In addition, operating time by the surgeon and staff is conserved by using the biphasic membranes of the invention.

The biphasic membrane of the invention also has the advantage that infection rates are decreased because excessive handling of the biomaterial and excessive shaping/cutting time is eliminated. As used herein, the term "lyphilization" refers to "freeze drying" or vacuum drying.

In the process for producing the membranes of the invention, the a molded collagen suspension is placed in a freezer and then a vacuum is applied. Under vacuum, the water within the collagen moves directly from the solid phase to the gas phase. Consequently, there is no shrinking or change to the dimensions. This makes a highly porous, but relatively weak collagen structure. A key step in the production process according to the invention is then to lightly wet the porous collagen with water which collapses the porosity. The material is then air dried. This makes a much stronger/stiffer collagen membrane. Air drying also crosslinks some of the collagen molecules to further increase the strength and decrease the resorption rate.

BRIEF DESCRIPTION OF THE FIGURES

The invention will be described in further detail hereinafter with reference to an illustrative example of a preferred embodiment shown in the accompanying figures, in which.

DETAILED DESCRIPTION OF THE INVENTION

Figure 1:
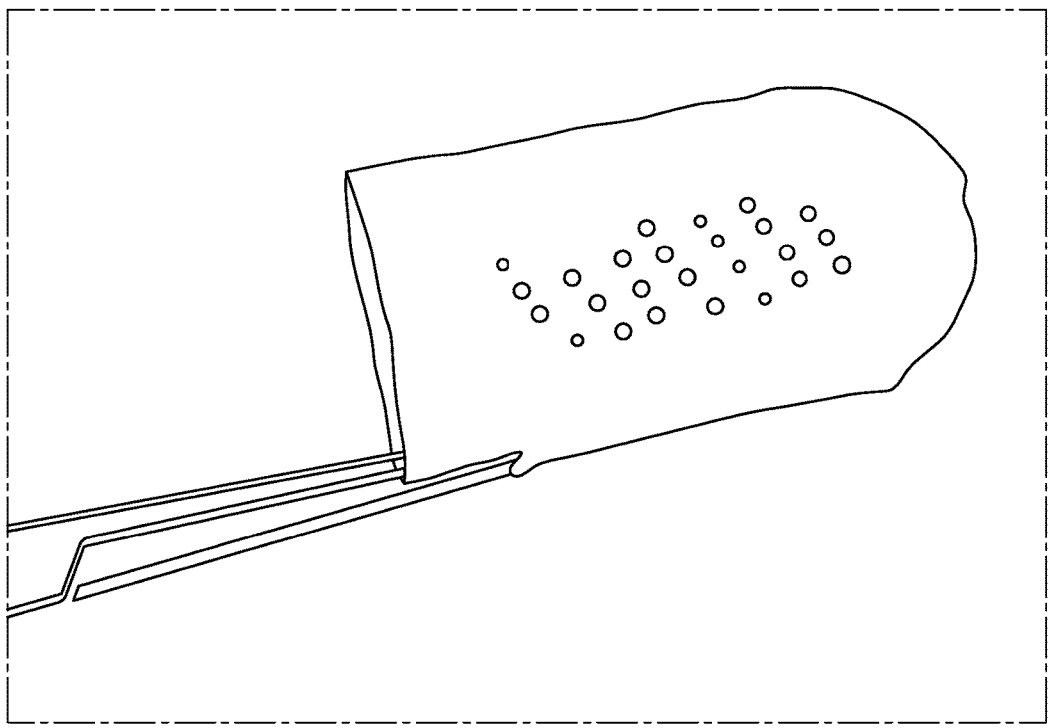
FIG. 1 is an illustration of a biphasic collagen socket capsule according to the present invention for use in repair of a buccal plate after tooth extraction.
Figure 2:
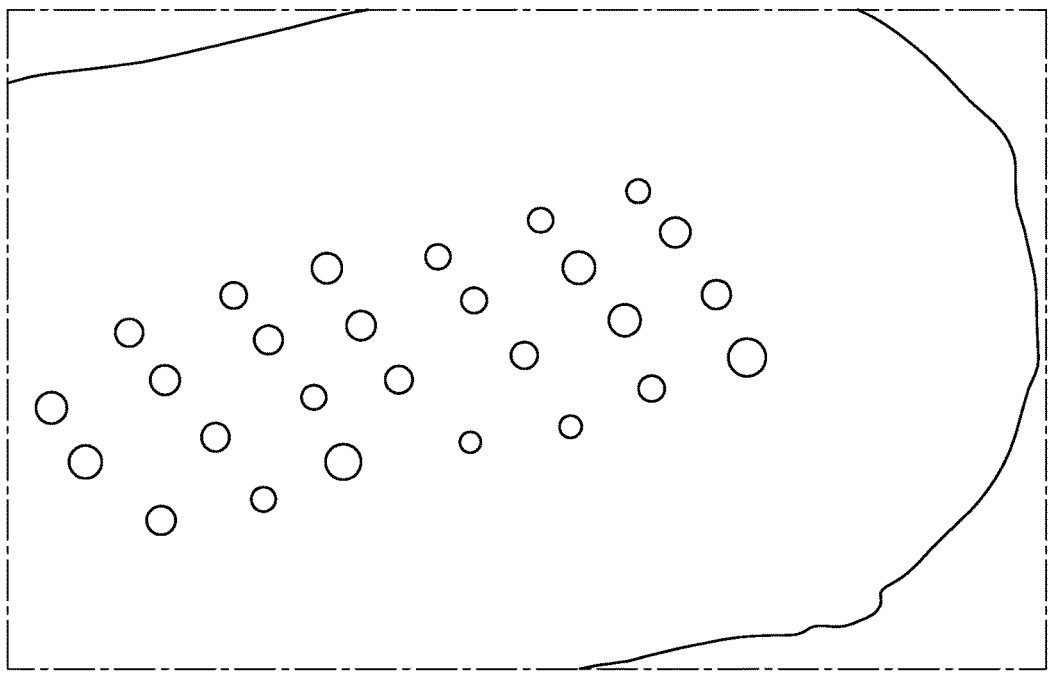
FIG. 2 is an enlarged illustration of the biphasic collagen socket capsule of FIG. 1 showing the perforations formed in the porous region of the membrane.

FIGS. 1 and 2 show a socket capsule according to the invention constructed of biphasic collagen for guided tissue regeneration in order to repair a buccal plate after tooth extraction.

A major problem encountered by dentists, particularly oral surgeons and periodontists, is restoration or regeneration of the buccal plate after tooth extraction. The buccal plate often becomes a thin layer of bone, particularly on the exterior surface (i.e., lip side) of the mandible or maxilla where it meets the teeth. If a natural tooth must be extracted because of a functional or cosmetic deviance, it may be replaced with a dental implant. Often, this buccal plate fractures during extraction or is resorbed. Dental implants require bone insertion depth to biologically anchor the metal surface into the mandible or maxilla. This biological process is called osteointegration. After tooth extraction, the surgeon must regenerate the amount of bone in the extraction socket and in buccal plate to at least the minimum depth to provide adequate osteointegration of the dental implant.

A capsule of relatively stiff, high density, low porosity collagen is ideal for containing bone grafting material and placing into the socket of an extracted tooth. The capsule restrains the bone grafting material to exactly the correct location for maximum bone formation. However, the low porosity of a capsule made of conventional collagen material may impede bone formation because bone formation requires neovascular ingrowth and osteoprogenitor cells from outside the capsule and the low porosity collagen material may act as a barrier against neovascular growth and migration of osteoprogenitor cells.

As a demonstration of this invention, capsules of bovine, Type 2 collagen were manufactured which are biphasic. The completed capsules are shown in FIGS. 1 and 2. The capsule can be filled with bone graft material such as autograft, allograft, growth factors, or ceramic particles. The apical portion and lingual side are formed with a matrix of perforations which give these regions a high porosity for facilitating neovascular ingrowth. The buccal portion has high stiffness to retain the bone graft material crestally. As a result of this advantageous capsule structure, when the capsule is filled with bone regenerating material and properly inserted into the socket of an extracted tooth, the buccal plate is restored with regenerated bone to the height desired by the surgeon.

The biphasic collagen capsules for guided tissue regeneration according to the invention were produced as follows:

Example 1: Casting

The first step is casting the basic capsule. A 10-60 mg/ml suspension of purified collagen in 5-25% alcohol/water is formed. A particularly preferred suspension contains 15 mg of collagen per ml of a 10% solution of ethanol in water. The collagen fibers preferably have a native fibrous structure and a length of from 0.2 to 3 mm, particularly preferably about 1.5 mm. After removing air bubbles from the suspension, a fixed amount of the suspension is poured into a mold comprised of mating male and female mold members which form a mold cavity between them. The mold cavity is completely filled with the collagen suspension, and the main frame of the mold is tightly attached to the elastic surface of bottom plate. A plurality of pins are then strategically extended through the female mold into the male mold. These pins serve as spacers for making the transmembrane, unidirectional holes in the membrane. Sufficient number of pins are placed to provide adequate neovascular ingrowth without compromising stiffness or strength. The pins may be arranged in any desired pattern which will produced the desired porosity. In the illustrated embodiment shown in the Figures, the pins are arranged in a generally rectangular array, but numerous other arrangement are also possible.

The filled mold was then placed in −70° C. freezer. After solidification of the collagen matrix, the pins were removed from the molds. Then one of the two vertical plates holding the frozen collagen was removed. The other vertical plate was also removed with the collagen on it. The plate with the frozen collagen was subsequently freeze-dried in a freeze-dryer.

The dried collagen was removed from the Freeze-dryer and sprayed with an alcohol solution. A preferred alcohol solution will contain 40 to 70% alcohol. A particularly preferred solution contains about 50% alcohol. The collagen material was then subjected to air drying followed by vacuum drying. The material was then heated at 100 to 140° C. for from 15 minutes to 2 hours. A preferred heat treatment is effected at 130° C. for 30 minutes. The heat treated collagen membrane was then removed and cut to the desired size.

Example 2: Penetration

The first step is casting the basic capsule. A 10-60 mg/ml suspension of purified collagen in 5-25% alcohol/water is formed. A particularly preferred suspension contains 15 mg of collagen per ml of a 10% solution of ethanol in water. The collagen fibers preferably have a native fibrous structure and a length of from 0.2 to 3 mm, particularly preferably about 1.5 mm. After removing air bubbles from the suspension, a fixed amount of the suspension is poured into a mold comprised of mating male and female mold members which form a mold cavity between them. The mold cavity is completely filled with the collagen suspension, and the main frame of the mold is tightly attached to the elastic surface of bottom plate.

The filled mold was then placed in −70° C. freezer. After solidification of the collagen matrix, the pins were removed from the molds. Then one of the two vertical plates holding the frozen collagen was removed. The other vertical plate was also removed with the collagen on it. The plate with the frozen collagen was subsequently freeze-dried in a freeze-dryer.

The dried collagen was removed from the Freeze-dryer and sprayed with an alcohol solution. A preferred alcohol solution will contain 40 to 70% alcohol. A particularly preferred solution contains about 50% alcohol. The collagen material was then subjected to air drying followed by vacuum drying. The material was then heated at 100 to 140° C. for from 15 minutes to 2 hours. A preferred heat treatment is effected at 130° C. for 30 minutes. The heat treated collagen membrane was then removed and cut to the desired size. Holes are then made in the membrane with strategically placed pins. The pins make the transmembrane, unidirectional holes in the membrane. Sufficient number of pins are placed to provide adequate neovascular ingrowth without compromising stiffness or strength. The pins may be arranged in any desired pattern which will produced the desired porosity. In the illustrated embodiment shown in the Figures, the pins are arranged in a generally rectangular array, but numerous other arrangement are also possible.

Example 3: Selective Rehydration/Drying

The first step is casting the basic capsule. A 10-60 mg/ml suspension of purified collagen in 5-25% alcohol/water is formed. A particularly preferred suspension contains 15 mg of collagen per ml of a 10% solution of ethanol in water. The collagen fibers preferably have a native fibrous structure and a length of from 0.2 to 3 mm, particularly preferably about 1.5 mm. After removing air bubbles from the suspension, a fixed amount of the suspension is poured into a mold comprised of mating male and female mold members which form a mold cavity between them. The mold cavity is completely filled with the collagen suspension, and the main frame of the mold is tightly attached to the elastic surface of bottom plate.

The filled mold was then placed in −70° C. freezer. After solidification of the collagen matrix, the pins were removed from the molds. Then one of the two vertical plates holding the frozen collagen was removed. The other vertical plate was also removed with the collagen on it. The plate with the frozen collagen was subsequently freeze-dried in a freeze-dryer. The dried collagen was removed from the Freeze-dryer and selected areas thereof were sprayed with an alcohol solution. A preferred alcohol solution will contain 40 to 70% alcohol. A particularly preferred solution contains about 50% alcohol. The areas that need to be high porosity are protected during the spraying operation. After the selected spraying of desired areas, the collagen material was then subjected to air drying followed by vacuum drying. The material was then heated at 100 to 140° C. for from 15 minutes to 2 hours. A preferred heat treatment is effected at 130° C. for 30 minutes. The heat treated collagen membrane was then removed and cut to the desired size.

The resulting capsule has areas of high tensile strength corresponding to the areas sprayed with the alcohol solution and other areas of lower tensile strength and higher porosity corresponding to the areas protected against spraying with the alcohol solution. The sprayed areas have a tensile strength of approximately 3600 g/mm$^2$ (35 MPa), a tensile modulus of approximately 95,000 g/mm$^2$ (932 MPa), pore diameters of less than 50 microns, and a porosity of less than 20%. In contrast, the protected areas have a tensile strength of only about 35 g/mm$^2$ (0.34 MPa), a tensile modulus of approximately 560 g/mm$^2$ (5.5 MPa), pore diameters of greater than 50 microns, and a porosity of more than 50%.

Example 4: Reverse Migration of Material

In another advantageous application of the biphasic membrane, a material may be introduced in interior of the collagen capsule or balloon and allow the material to migrate from the inside to the outside. This is essentially the opposite of the procedure described above. An example of having a material move from the inside to the outside is bone cement. Bone cement is a methyl-methacrylate based, non-resorbable biomaterial used to fix hip and knee metal implants. There are also some resorbable calcium based bone cements. Both of these types of cements are used to fix certain fractures, particularly spinal vertebral body fractures. In some cases, a large hole is made in the vertebral body with a removable, standard rubber balloon, similar to an angioplasty balloon or a sinus balloon. Bone cement is then injected into the hole to fix the fracture. An application of the biphasic collagen balloon is to be able to direct the location of the cement. The cement may selectively penetrate through the holes, particularly where it is weaker than the less porous areas to make adhesive contact with the surrounding bone tissue at specifically desired locations.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A biocompatible, resorbable biphasic collagen membrane in the form of a capsule for use in guided tissue regeneration comprising a first portion and a second portion, said first portion comprising transmembrane unidirectional holes and having relatively lower tensile strength and stiffness and higher porosity as compared to said second portion and said second portion being free of transmembrane unidirectional holes and having relatively higher tensile strength and stiffness and lower porosity as compared to said first portion, wherein said holes are strategically positioned in said membrane in a pattern to provide the desired porosity, to control placement of bone regenerating material and thus guide the development of new or additional bone.

2. A membrane as claimed in claim 1, wherein said membrane is formed of collagen fibers having a native fibrous structure and a fiber length of from 0.2 to 3 millimeters.

3. A membrane as claimed in claim 2, wherein said fibers have an average length of about 1.5 millimeters.

4. A membrane as claimed in claim 1, wherein said second portion has a tensile strength of approximately 3600 g/mm$^2$, a tensile modulus of approximately 95,000 g/mm$^2$ pore diameters of less than 50 microns, and a porosity of less than 20%, and said first portion has a tensile strength of about 35 g/mm$^2$, a tensile modulus of approximately 560 g/mm$^2$, pore diameters of greater than 50 microns, and a porosity of more than 50%.

* * * * *